United States Patent
Weikel et al.

(10) Patent No.: US 6,306,514 B1
(45) Date of Patent: *Oct. 23, 2001

(54) SLIP-COATED ELASTOMERIC FLEXIBLE ARTICLES AND THEIR METHOD OF MANUFACTURE

(75) Inventors: William Joseph Weikel, Arlington; John W. Bulluck, Spicewood, both of TX (US)

(73) Assignee: Ansell Healthcare Products Inc., Red Bank, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/777,105

(22) Filed: Dec. 31, 1996

(51) Int. Cl.[7] ................................................. B32B 13/12
(52) U.S. Cl. ...................................... 428/451; 264/211.24
(58) Field of Search ....................... 264/211.24; 428/451

(56) References Cited

U.S. PATENT DOCUMENTS

| | | | |
|---|---|---|---|
| 3,251,905 | 5/1966 | Zelinski | 260/879 |
| 3,265,765 | 8/1966 | Holden et al. | 260/876 |
| 3,268,593 | 8/1966 | Carpenter et al. | 260/615 |
| 3,286,011 | 11/1966 | Kavalir et al. | 264/306 |
| 3,293,191 | 12/1966 | Carpenter et al. | 252/351 |
| 3,390,207 | 6/1968 | Moss et al. | 260/879 |
| 3,411,982 | 11/1968 | Kavalir et al. | 161/242 |
| 3,598,887 | 8/1971 | Darcy et al. | 260/879 |
| 3,639,521 | 2/1972 | Haieh | 260/880 |
| 3,740,262 | 6/1973 | Agostinelli | 117/94 |
| 3,813,695 | 6/1974 | Podell, Jr. et al. | 2/168 |
| 3,856,561 | 12/1974 | Esemplare et al. | 117/139 |
| 3,905,823 | 9/1975 | Piskoti | 106/38.22 |
| 3,992,221 | 11/1976 | Homsy et al. | 134/16 |
| 4,070,713 | 1/1978 | Stockum | 2/168 |
| 4,082,862 | 4/1978 | Esemplare et al. | 427/133 |
| 4,143,109 | 3/1979 | Stockum | 264/112 |
| 4,208,356 | 6/1980 | Fukawo et al. | 525/89 |
| 4,219,627 | 8/1980 | Halasa et al. | 525/89 |
| 4,302,852 | 12/1981 | Joung | 2/167 |
| 4,310,928 | 1/1982 | Joung | 2/161 |
| 4,482,577 | 11/1984 | Goldstein et al. | 427/2 |
| 4,499,154 | 2/1985 | James et al. | 428/494 |
| 4,548,844 | 10/1985 | Podell et al. | 428/35 |
| 4,575,476 | 3/1986 | Podell et al. | 428/494 |
| 4,597,108 | 7/1986 | Momose | 2/168 |
| 4,690,955 | 9/1987 | Kilgour et al. | 521/112 |

(List continued on next page.)

FOREIGN PATENT DOCUMENTS

| | | |
|---|---|---|
| 365547 | 1/1932 | (GB) . |
| 1254093 | 11/1971 | (GB) . |
| 8100361 | 2/1981 | (WO) . |

OTHER PUBLICATIONS

"Special Report; Raw Materials; Additives," *Chemical Week*, Oct. 12, 1994; p. 46.

"Product Array Broadens; Demand, For High Performance Rises," by Esther D'Amico, *Chemical Week*, Oct. 11, 1995, p. 39.

"OSI Specialties, Inc.: a New Global Company Brings Over Four Decades of Leadership to the Nonwovens Finishing Marketplace; 12th Annual International Show in Print," *Nonwovens Industry*, May 1994, vol. 25; No. 5; p. 100.

*The Vanderbilt Latex Handbook*, edited by Robert Francis Mausser, Third Edition, Published by R.T. Vanderbilt Company, Inc., pp. 208–210.

*Neoprene Latex*, by John Carl, E.I. DuPont, Wilmington, DE, 1962 (one page).

Technical Summary Sheet—Zeneca: NeoRez XR–9624, Experimental Water–borne Polyruethane, Revised 1/94 (4 pages).

"The Importance of Low Dynamic Surface Tension in Waterborne Coatings," by Joel Schwartz, *Journal of Coatings Technology*, Sep. 1992 (11 pages plus cover page).

"Antifoam, Plastics, Additives and Other Processes," *Silicones*, vol. II; Chemical Technology Review No. 92, pp. 344–347 plus cover page.

(List continued on next page.)

*Primary Examiner*—Terressa Mosley
(74) *Attorney, Agent, or Firm*—Gardner, Carton & Douglas

(57) ABSTRACT

In accordance with the present invention, there is provided an elastomeric flexible article, such as a surgeon's glove, and its method of manufacture. A flexible elastomeric article has a wearer-contacting surface in which a lubricant composition has been applied so as to substantially improve the lubricity of the surface with respect to damp skin. The lubricant composition is selected from the group consisting of a first composition and a second composition. The first composition comprises an acetylenic diol and at least one compound selected from the group consisting of an organo-modified silicone, an amino-modified silicone, and a cationic surfactant. The second composition comprises a cationic surfactant and at least one compound selected from the group consisting of an organo-modified silicone, an amino-modified silicone, an amino-modified silicone, and an acetylenic diol. The method of manufacturing the elastomeric flexible article comprises the following steps. Coating the article surface with an acrylic-type resin which contains styrene. Curing the resin coating. Halogenating at least one surface of the article. Neutralizing the article surface. Treating the article surface with a lubricant composition. The lubricant composition is selected from the group consisting of a first composition and a second composition. The first composition comprises an acetylenic diol and at least one compound selected from the group consisting of an organo-modified silicone, an amino-modified silicone, and a cationic surfactant. The second composition comprises a cationic surfactant and at least one compound selected from the group consisting of an organo-modified silicone, an amino-modified silicone, and an acetylenic diol.

19 Claims, No Drawings

U.S. PATENT DOCUMENTS

| | | | |
|---|---|---|---|
| 4,769,174 | 9/1988 | Kilgour | 252/351 |
| 4,847,398 | 7/1989 | Mehta et al. | 556/445 |
| 4,851,266 | 7/1989 | Momose et al. | 427/353 |
| 4,857,583 | 8/1989 | Austin et al. | 524/761 |
| 5,284,607 * | 2/1994 | Chen | 264/37 |
| 5,395,666 | 3/1995 | Brindle | 429/36.4 |
| 5,570,475 | 11/1996 | Nile et al. | 2/161.7 |
| 5,691,069 | 11/1997 | Lee | 428/500 |

OTHER PUBLICATIONS

*High Polymer Latices*, by D. C. Blackley, vol. 2, Testing and Applications, Palmerton Publishing Co. Inc. 1966, p. 548.

Material Safety Data Sheet—Sigma Chemical Company: Cetylpyridinium Chloride Crystalline (5 pages).

Material Safety Data Sheet—OSi Specialties, Inc.: NUWET 300, Feb. 9, 1995 (5 pages).

Technical Summary Sheet—Air Products and Chemicals, Inc.: DYNOL* 604 SURFACTANT (9 pages).

Technical Summary Sheet—OSi Specialties: NuWet Durable Hydrophilic Finishes for Nonwovens (14 pages).

Technical Summary Sheet—OSi Specialties: NuWet Hydrophilic Silicone Finishes Using Aqueous and Nonaqueous Diluents (30 pages).

Material Safety Data Sheet—Van Waters & Rogers Inc., Subsidiary of Univar: Silicone Emulsion LE–46, pp. 1–4).

Material Safety Data Sheet—Zeneca: NeoRaz R–962 (3 pages).

"Acetylenic Diol–Based Additives Help Glove Makers Meet Quality Standards," by Joel Schwartz and William R. Dougherty, *Elastomerics*, Dec. 1989, pp. 16–18.

USSN 08/699,032, filed Aug. 19, 1996, "Elastomeric Flexible Articles and Their Method of Manufacture", pending.

* cited by examiner

SLIP-COATED ELASTOMERIC FLEXIBLE ARTICLES AND THEIR METHOD OF MANUFACTURE

CROSS-REFERENCE TO RELATED APPLICATION

This application is related to copending U.S. application Ser. No. 08/673,302, filed on Jun. 28, 1996 and entitled "Elastomeric Flexible Articles and Their Method of Manufacture," and U.S. application Ser. No. 08/699,032, filed on Aug. 19, 1996 and entitled "Elastomeric Flexible Articles and Their Method of Manufacture," both assigned to a common assignee.

TECHNICAL FIELD OF THE INVENTION

This invention relates to elastomeric flexible articles (e.g., film articles), particularly powder-free medical gloves, that exhibit enhanced lubricity ("slip") with respect to both dry and damp surfaces, particularly skin or other tissue of the wearer, as compared to similar articles or films that are not treated as described herein. This invention also relates to a process for making such articles. This invention further relates to a method of treating elastomeric flexible articles with a slip coating and optionally further treating with a lubricant composition.

BACKGROUND OF THE INVENTION

Elastomeric surfaces of articles, in general, exhibit poor lubricity with respect to a dry surface, such as dry skin or other mammalian tissue. These properties are due to surface friction. Additionally, many elastomeric articles or surfaces display poor lubricity with respect to damp surfaces. A high coefficient of friction is a distinct disadvantage in those applications where an elastomeric surface must slide on another surface, such as in the donning of gloves over dry or damp skin. This is particularly important in the use of medical gloves, such as examination gloves and surgeon's glove. These gloves are relatively close fitting in order to provide sensitivity. Further, most surgeons don their gloves after scrubbing up and without having fully dried their hands, so that their hands may be distinctly damp. Accordingly, the elastomeric materials useful in such applications must exhibit enhanced lubricity with respect to dry surfaces ("dry slip"), enhanced lubricity with respect to damp surfaces ("damp slip"), and the requisite mechanical properties. The prior art has attempted various ways to produce powderless gloves which satisfy these requirements.

One prior approach is to halogenate the surface of rubber gloves with chlorine or bromine to make it slippery, i.e., reducing tackiness and decreasing the coefficient of friction of the rubber gloves. In the case of chlorine as the halogen, the prior art discloses the production and use of chlorinated water to treat the rubber gloves. Such methods include (1) direct injection of chlorine gas into the water mixture, (2) mixing high density bleaching powder and aluminum chloride in water, (3) brine electrolysis to produce chlorinated water, and (4) acidified bleach. See for example U.S. Pat. No. 3,411,982 (Kavalir), U.S. Pat. No. 3,740,262 (Agostinelli), U.S. Pat. No. 3,992,221 (Homsy, et al.; treating outer surface with chlorine gas), U.S. Pat. No. 4,597,108 (Momose), and U.S. Pat. No. 4,851,266 (Momose). However, chlorination produces surfaces which have very poor damp slip.

There are other prior rubber gloves having a slip layer bonded to the inner surface of such gloves. Examples of gloves which have an inner layer of elastomeric material with particulate lubricant imbedded therein are disclosed in U.S. Pat. No. 4,070,713 (Stockum), U.S. Pat. No. 4,143,109 (Stockum), U.S. Pat. No. 5,284,607 (Chen) and U.S. Pat. No. 5,395,666 (Brindle; together with a surfactant, but ionic surfactants are not recommended), and which disclose surgeon's gloves with various polymeric slip coatings bonded to the inner surface thereof are U.S. Pat. Nos. 3,286,011 and 3,411,982(both to Kavalir et al.; an inner layer of a rubber/ resin combination, wherein the resin maybe acrylic-type resins, allowing elongation values of 200% to 700%) ; U.S. Pat. No. 3,813,695 (Podell, et al.; an inner layer of hydrophilic plastic material, e.g., hydrogel polymer), U.S. Pat. No. 3,856,561 (Esemplare, et al.; an inner layer of a copolymer of vinyl or vinylidene chloride and an alkyl acrylate, e.g., copolymer of vinyl chloride or vinylidene chloride with butyl acrylate and acrylic acid), U.S. Pat. No. 4,302,852 (Joung; e.g., inner layer of silicone), U.S. Pat. No. 4,482,577 (Goldstein, et al.; elastomeric article is cleaned, immersed in a concentrated solution of a strong acid, washed, dipped in a solution of an uncured hydrophilic polymer and then cured; articles are described as stretchable to 700%), U.S. Pat. No. 4,499,154 (James, et al.; article is pre-treated in a dilute acid solution prior to applying inner layer; uses specific hydrogel polymers as the inner layer which is then treated with a cationic surfactant or fatty amine) and U.S. Pat. No. 4,575,476 (Podell, et al.; hydrogel polymer inner layer treated with cationic, anionic or nonionic surfactant).

Some of the latter-type gloves experience delamination of the layers or produce a "cobblestoning" effect when stretched, for example, when the gloves are donned. Prior gloves have been made to address this problem. According to U.S. Pat. No. 5,570,475, prior attempts to improve resistance to delamination have included treatment of the natural or synthetic elastomeric base material by an acid priming step and a neutralizing step prior to the polymer coating step, citing U.S. Pat. No. 4,499,154 (noted above). According to U.S. Pat. No. 4,548,844 (Podell et al.), a trivalent cationic salt, e.g., aluminum salt, may be applied to the elastomeric article prior to or simultaneously with the application of the hydrophilic hydrogel polymer so as to provide for improved adhesion of the polymer to the article after curing. Others gloves utilize certain types of polymers as the inner layer to avoid or minimize delamination when the article is stretched or flexed. For example, U.S. Pat. No. 4,082,862 (Esemplare et al.) is identified as an improvement over U.S. Pat. No. 3,856,561 (Esemplare et al.) to avoid the "cobblestoning" effect observed when the elastomeric article is stretched to a large extent, e.g., over 450%. Therein, a blend of polymers each with specific required properties is used. As another example, U.S. Pat. No. 5,570,475 (Nile et al.) discloses copolymers of styrene or ethylene with half esters of maleic acid.

The foregoing differ from the present invention.

SUMMARY OF THE INVENTION

In accordance with the present invention, there is provided a flexible article displaying slip properties with respect to damp and dry mammalian tissue without use of powder lubricants. The article is comprised of a substrate layer having an elastomeric material, the substrate layer having a first surface and a second surface, a crosslinked polymer coating, the coating having a third surface and a fourth surface, wherein the third surface of the coating is covalently bonded to the second surface of the substrate layer and, optionally, a damp slip-conferring amount of a lubricant composition applied to the fourth surface of the coating. The coating is non-blocking, exhibits excellent adhesion to the substrate layer even at high elongation values and also exhibits excellent dry slip during, for example, donning of a surgeon's glove. The lubricant composition confers excellent damp/wet slip during, for example, damp/wet donning of a surgeon's glove.

There is also provided a method of treating an elastomeric flexible article. The method involved in producing the coated elastomeric articles is a multistep procedure which includes (1) forming an elastomeric article, (2) priming the surface of the elastomer with an acidic solution, (3)coating the elastomer surface with a non-blocking, slip-conferring polymer solution, (4) curing the elastomer and the polymer, (5) chlorinating at least the wearer-contacting surface of the coated article, (6) neutralizing the article surface and residual chlorine, and, optionally, (7) treating the wearer-contacting surface with a lubricant composition to enhance the damp/wet slip properties thereof.

An important feature of this invention is that the slip coating exhibits tremendous adhesion to elastomeric substrates even when such substrates are elongated to break. These coatings are prepared from a coating bath composition containing (1) an acrylic-type resin which may contain reactive functional groups such as carboxyl, hydroxyl, amide and methylol groups and which may be a copolymer made using styrene, acrylonitrile and/or an alkylene monomer and which may be self-reactive (i.e., that a crosslinker is not required for crosslinking thereof); (2) a metal salt; (3) an acid catalyst; and (4) a highly reactive crosslinking agent (which is optional if the resin is self reactive). The acrylic-type resins contain adequate functionality when combined with an effective amount of the crosslinking agent (unless the resin is self-reactive, then an effective amount of reactive functional groups) to effect curing thereof. The crosslinkers employed in this invention are typically reactive toward thiol, carboxyl, amide, and hydroxyl groups. The metal salt also acts as a coagulant for the resin thus resulting in an effective deposition of the coating onto the elastomeric substrate. The crosslinking of the coating also results in either immobilizing or creating a barrier to the migration of the proteins and curatives in the elastomeric substrate which can sometimes be allergenic. Such materials are typically leached out by the users sweat, but since the coating is water resistant, the sweat is prevented or at least inhibited from leaching such components from the elastomeric substrate.

The slip coating provided by the present invention has excellent characteristics of slipperiness. A simple way to demonstrate the slipperiness of this coating is to place two coated rubber surfaces together and rub the contacting surfaces back and forth while grasped between the fingers. Previous slip coatings which have been tested do not slip at all or with difficulty when held in this manner. However, the coatings provided by the present invention readily slip irrespective of the amount of grasping pressure applied.

The coatings produced by the present invention are highly durable and water resistant. This is a desirable feature since elastomeric articles, specifically natural rubber latex medical devices, may be subjected to rigorous washing and autoclaving steps to remove the allergenic constituents from the articles. The articles may also be subjected to a chlorination step. The coatings provided by the present invention are unaffected by such treatments.

The elastomeric articles of the present invention are provided with a non-blocking surface thus eliminating the need for application of a post-cure powder slurry as is commonly employed on conventional elastomeric articles.

Furthermore, the coating may be formulated from a variety of commercially available water-based acrylics including styrene acrylics or acrylic acrylonitrile lattices. These lattices are applied to the elastomeric articles as an aqueous resin containing a water-soluble crosslinking agent such as a melamine, urea-formaldehyde, or glycoluridil commercial crosslinker. The use of water-based commercially available materials is an advantage since this leads to reduced manufacturing costs, low VOCs (volatile organic compounds), and increased worker safety.

The elastomer of the substrate layer can be either a natural or a synthetic elastomer, or a combination thereof. The elastomer is preferably selected from the group consisting of natural rubber, a polyurethane, a homopolymer of a conjugated diene, a copolymer of at least two conjugated dienes, a copolymer of at least one conjugated diene and at least one vinyl monomer and combinations thereof. The conjugated diene may contain hetero atoms, such as conjugated dienes which have been halogenated, e.g., chloroprene. Preferred conjugated dienes include butadiene, isoprene, piperylene and chloroprene. Preferred vinyl monomers include alkenyl arenes, e.g., styrene; alkylenes, e.g., ethylene and propylene; and acrylonitrile. The term "combinations thereof" in regard to the elastomer includes physical combinations thereof in a single layer and layered combinations thereof, for example, a multi-layered elastomeric article having a layer of polyurethane formed over and adhering to a layer of natural rubber.

The lubricant composition has a silicone surfactant and at least one organic surfactant. The silicone surfactant may be a non-modified or modified silicone. The organic surfactant may be any such surfactant compatible with the silicone surfactant. Preferably, the organic surfactant is a cationic surfactant, e.g., 1-hexadecylpyridinium chloride monohydrate (also known as cetylpyridinium chloride or CPC).

In one embodiment, the article is a surgeon's glove. Medical powder-free gloves having the cured resin coating have good dry donning and resistant to delamination, and if further treated with the lubricant composition provide superior lubricity with respect to wet/damp donning in comparison to the current chlorinated surgical gloves in the market.

DETAILED DESCRIPTION OF THE INVENTION

The invention envisages flexible elastomeric articles including those adapted for use in partial or total contact with mammalian tissue, such as surgical, examination and dental gloves, condoms, bandages, catheters, ureters, sheathes and sheath-type incontinence devices and other film articles. Additionally, the damp/dry slip-conferring materials may be provided on one or more surfaces of the article including, but not limited to, an inner and/or outer surface relative to the wearer, as appropriate under the circumstances of the use of each article.

For purposes of this description, the outer surface of an article and, in particular, a glove, is defined as that surface which becomes an external surface of the glove in the position of actual use when worn. The inner surface is defined as that surface which is adjacent to the skin of the wearer when worn. The reverse is true in the case of a catheter or ureter: the outer surface is the surface in contact with the wearer's tissue. To avoid ambiguity, the term "wearer-contacting surface" will be used herein. "Tissue" includes skin or epithelia without limitation.

The elastomer used in the substrate layer may be a natural or synthetic rubber. Without limitation, synthetic rubbers include polyurethane, a homopolymer of a conjugated diene, a copolymer of at least two conjugated dienes, a copolymer of at least one conjugated diene and at least one vinyl monomer, and combinations thereof.

The conjugated dienes are preferably ones containing from 4 to 8 carbon atoms. Examples of such suitable conjugated dienes include: 1,3-butadiene (butadiene), 2-methyl-1,3-butadiene (isoprene), 2,3-dimethyl-1,3-butadiene, 1,3-pentadiene (piperylene), 1,3-hexadiene, and the like. The conjugated dienes may contain hetero atoms. Such conjugated dienes include those which have been halogenated, for example, chloroprene. Mixtures of such conjugated dienes may also be used. The preferred conjugated dienes are butadiene, isoprene and chloroprene.

Any vinyl monomer may be used for copolymerization with at least one conjugated diene to prepare synthetic rubbers so long as the resulting copolymer is elastomeric. Without limitation, such vinyl monomers include alkylenes, alkenyl arenes, and acrylonitrile. The preferred alkylenes are ethylene, propylene and butylenes. The preferred alkenyl arenes are monoalkenyl arenes. The term "monoalkenyl arene" will be taken to include particularly those of the benzene series such as styrene and its analogs and homologs including o-methylstyrene, p-methylstyrene, p-tert-butylstyrene, 1,3-dimethylstyrene, alpha-methylstyrene and other ring alkylated styrenes, particularly ring-methylated styrenes, and other monoalkenyl polycyclic aromatic compounds such as vinyl naphthalene, vinyl anthracene and the like. The preferred monoalkenyl arenes are monovinyl monocyclic arenes such as styrene and alpha-methylstyrene, and styrene is particularly preferred.

The copolymers may be random, tapered or block copolymers. If the copolymers are block copolymers, it will be understood that each of the blocks thereof may be a homopolymer, a random copolymer or a tapered copolymer as long as each block predominates in at least one class of the monomers characterizing the block. For example, blocks of alkenyl arenes may comprise styrene/alpha-methylstyrene copolymer blocks or styrene/butadiene random or tapered copolymer blocks as long as the blocks individually predominate in alkenyl arenes.

Preferred rubbers are natural rubber and synthetic rubbers, including polyurethane, neoprene, nitrile rubber, block copolymers of styrene and butadiene, particularly a styrene-butadiene-styrene block copolymer, and block copolymers of styrene and isoprene, particularly a styrene-isoprene-styrene block copolymer. Natural rubber and polyurethane are more preferred, with natural rubber being most preferred. Neoprene is a homopolymer of the conjugated diene chloroprene. Nitrile rubber is a copolymer of the conjugated diene butadiene and the vinyl monomer acrylonitrile.

The block copolymers of alkenyl arenes ("A" blocks) and conjugated dienes ("B" blocks) are preferably network forming, i.e., at least two A blocks and at least one B block. The simplest form of such a block copolymer is A-B-A, which is a triblock copolymer. In such a synthetic rubber, the A blocks are thermodynamically incompatible with the B block(s) resulting in a rubber consisting of two phases; a continuous elastomeric phase (B blocks) and a basically discontinuous hard, glass-like plastic phase (A blocks) called domains. These domains act as physical crosslinks anchoring the ends of many block copolymer chains. Since the A-B-A block copolymers have two A blocks separated by a B block, domain formation results in effectively locking the B blocks and their inherent entanglements in place by the A blocks and forming a network structure. Such a phenomenon allows the A-B-A rubber to behave like a conventionally vulcanized rubber that contains dispersed reactive filler particles. These thermoplastic A-B-A rubbers are physically crosslinked by the domains in a network structure as opposed to being chemically crosslinked like a conventionally vulcanized rubber. As such, these polymers may be handled in thermoplastic forming equipment and are soluble in a variety of relatively low cost solvents. Additionally, when polymers of this type are used, the vulcanization step may be eliminated and, contrary to vulcanized scrap rubbers, the scrap from the processing of these thermoplastic elastomers can be recycled for further use.

The block copolymers may be produced by any well known block polymerization or copolymerization procedures including the well known sequential addition of monomer techniques, incremental addition of monomer technique or coupling technique as illustrated in, for example, U.S. Pat. Nos. 3,251,905; 3,390,207, 3,598,887 and 4,219,627, the disclosures of which are incorporated herein by reference. As is well known in the block copolymer art, tapered copolymer blocks can be incorporated in the multiblock copolymer by copolymerizing a mixture of conjugated diene and alkenyl arene monomers utilizing the difference in their copolymerization reactivity rates. Various patents describe the preparation of multiblock copolymers containing tapered copolymer blocks including U.S. Pat. Nos. 3,251,905; 3,265,765; 3,639,521 and 4,208,356, the disclosures of which are incorporated herein by reference.

It should be observed that the above-described polymers and copolymers may, if desired, be readily prepared by the methods set forth above. However, since many of these polymers and copolymers are commercially available, for example, KRATON® polymers available from Shell Oil Company, it is usually preferred to employ the commercially available polymer as this serves to reduce the number of processing steps involved in the overall process.

Typical thicknesses of the elastomeric substrate layer for surgical gloves range from about 15 to about 400 microns, preferably from about 100 to about 350 microns. Surgical gloves tend to be about 150 microns thick and orthopedic gloves tend to be about 300 microns thick.

To confer both dry and damp slip to the coated elastomeric article, the substrate is treated using a multiple step process involving (1) coating with an acrylic-type resin coating solution, (2) curing the coating and substrate, (3) chlorinating the article, and (4) surfactant treating the article with a lubricant composition containing a silicone and organic surfactants. The resultant elastomeric products are powderfree and highly lubricious.

The elastomeric surface may be prepared prior to coating in a priming step by acid treating or other surface preparation techniques in order to insure excellent adhesion between the coating and the elastomeric substrate. Polymer surfaces are often difficult to bond to because of low surface energy, contamination, and the bloom of plasticizers or low molecular weight compounds. Other methods of preparing the elastomeric surface may include but is not limited to plasma treatment, corona treatment, ozone treatment, or chemical priming of the elastomer. The coating system exhibits excellent adhesion even when the elastomeric article is highly elongated.

Acid Pretreatment Step Alternative Methods

By way of example, gloves according to the present invention have been prepared gloves using two distinct acid surface preparation techniques including treating the latex with a 2% sulfuric acid predip prior to rinse and overcoating with the coating solution. An alternate method of surface preparation involved acidification of the leach prior to overcoating. To the leach water was added about 0.25% by weight of concentrated sulfuric acid and the gloves were placed in the leach tank for about twelve minutes at about 110° F. Both procedures produced gloves that have coatings with excellent adhesion. The excellent adhesion of the coating was evident when the coated latex article was elongated four hundred percent (400%) and no delamination of the coating occurred.

As has been discussed, the coating has an acrylic type resin, crosslinking agent, metal salt and an acid catalyst. The following is a discussion of the preferred embodiments pertaining to each of the aforementioned components.

A number of acrylic emulsions or dispersions have been found suitable in producing highly adherent coating surfaces on the elastomeric articles. The acrylic emulsions evaluated contain residual unreacted groups such as carboxyl or hydroxyl. Suitable acrylic resins, the styrene-acrylic resins, or acrylonitrile-modified acrylics resins NP-32 and Rhoplex® AC-3094, AC-2573, and AC-1024 available from Rohm and Haas Co., Philadelphia, Pa.; Carboset® 531 and Carboset® GA-1594, available from B.F. Goodrich Speciality Chemicals, Cleveland, Ohio; and UCAR® Latex 413, and UCAR Latex 452 available from UCAR Emulsion Systems, Union Carbide Corp., Cary, N.C.

| PRODUCT | FUNCT-IONALITY | SURFACTANT SYSTEM | COMPOSITION |
| --- | --- | --- | --- |
| ROHM & HAAS NP-32 | carboxyl | nonionic | 46% solids; self-crosslinking acrylic emulsion |
| ROHM & HAAS AC-3094 | carboxyl and hydroxyl | nonionic | 47% solids; acrylic emulsion |
| ROHM & HAAS AC-2573 | carboxyl | nonionic | 46% solids; acrylic emulsion |
| ROHM & HAAS AC-1024 | carboxyl and hydroxyl | nonionic and anionic | 50% solids; styrene acrylic copolymer |
| CARBOSET® 531 | carboxyl | not available | 25% solids; self-crosslinking styrene acrylic copolymer |
| CARBOSET® GA-1594 | carboxyl | not available | 40% solids; styrene acrylic copolymer |
| UCAR® 452 (styrene-acrylic latex) | hydroxyl and carboxyl | nonionic, Nonyl phenoxy poly (ethyleneoxy) ethanol | 44% solids; copolymer of butyl acrylate, acrylonitrile and methacrylic acid (CAS #27401-61-2) and copolymer of styrene, ethyl acrylate, methacrylic acid, and |

-continued

| PRODUCT | FUNCT-IONALITY | SURFACTANT SYSTEM | COMPOSITION |
| --- | --- | --- | --- |
| UCAR® 413 | carboxyl | nonionic, nonylphenoxy poly(ethyleneoxy) ethanol (CAS #9016-45-9) | hydroxyethylacrylate (CAS #29828-29-3) 47% solids; copolymer of butyl acrylate, methyl methacrylate, and methacrylic acid (CAS #25035-69-2) |

The specific compositions of the Rohm & Haas, UCAR®, and Carboset® acrylic copolymer products are considered proprietary. Most suitable monomers for these emulsion products exhibit low water solubility. Other monomers such as methacrylic acids and acrylic acids may be included to improve the adhesion characteristics of these emulsions. Available surfactants used for these emulsions are anionic, cationic, and nonionic. Mixed anionic and nonionic surfactants are the most commonly used in acrylic emulsions. Cationic surfactants are rarely used however when used they are the quaternary ammonium halide salt type. Typical constituents in acrylic copolymer emulsions are given below:

Anionic Surfactants
Stearate Soaps
Dodecyl benzene sulphonate
Sodium Dioctyl sulphosuccinate Cationic Surfactants
Cetyl trimethyl ammonium bromide Nonionic Surfactants
Polyethoxylated nonyl phenol
Polyethoxylated polypropylene glycol Emulsion polymers are two phase systems of two immiscible liquids, small droplets of polymer are the dispersed phase and water is the continuous phase. It is believed that while monomers can combine during polymerization in a variety of configurations including random, block, alternating and graft the vast majority of these acrylic polymers that are used in coatings are random. The random configuration decreases tenacity and crystallization not desirable in acrylic copolymer coating polymers. Self crosslinking of these emulsions can be accomplished by incorporating an acrylamide or an alkoxy methyl acrylamide into the polymer backbone. The acrylamide modified acrylics require a baking schedule of approximately 20 to 30 minutes at 150–180° C.

The preferred crosslinkers are the melamines which may be polymeric or monomeric and methylated or non-methylated. Suitable melamines that functioned effectively as crosslinkers and commercially available were the Cymel® 373, Cymel® 350, and Cymel® 303 available from Cytec Industries, West Patterson, N.J., and the Astro Industries Aricel PC-5, and Monsanto's Resimine® 797. Glycoluridil crosslinkers may also be used in the present invention, for example, Cymel® 1171 and 1172 available from Cytec Industries, West Patterson, N.J. produced excellent coatings on the elastomeric substrates. Urea-formaldehydes were found to effectively function as crosslinkers, for example, the Beetle Resins such as Beetle® 65 was found effective.

CROSSLINKER CHARACTERIZATION

| TYPE | METHYLATED MELAMINE CYMEL ® 373, Resimine 797, AND CYMEL ® 350) | METHYLATED UREA FORMALDEHYDE (BEETLE 65) | GLYCOLURILS (CYMEL ® 1172) AND (CYMEL 1171) | MELAMINES FULLY ALKYLATED (CYMEL ® 300 AND 303) Aricel ® PC-5 |
|---|---|---|---|---|
| REACTIVE WITH: | | | | |
| HYDROXY GROUPS | YES | YES | YES | YES |
| CARBOXYL GROUPS | YES | SLIGHT | YES | YES |
| AMIDE GROUPS | YES | YES | YES | YES |
| TYPICAL CURE TEMPERATURES | ELEVATED TEMPERATURE (250° F.) | ROOM TEMPERATURE | ELEVATED TEMPERATURE (200° F.) | ELEVATED TEMPERATURE (45° C.) |
| CATALYST NEEDED | LIKELY | NO | YES | YES | one function of the metal salt is to serve as a coagulant which is in part responsible for the remarkable adhesion observed for the coating. The aluminum nitrate acts as a coagulant for the latex and as a catalyst for the crosslinking of the melamine. A number of metal salt catalysts exist that fulfill the requirements described in the present invention. Amongst these are magnesium bromide, aluminum sulfate, aluminum nitrate, zinc nitrate, magnesium nitrate, silver nitrate, and zirconium complexes. The metal nitrates are preferred due to their excellent water solubility.

A number of acid catalysts were evaluated in the formulations to insure complete curing of the acrylic coatings within the temperature and time constraints of the elastomeric articles. The catalysts evaluated were as follows: Cycat® 4040, Cycat® 600, Phosphoric acid, Nacure® 1419, Nacure® 1953, and Nacure® 3525. The catalyst are chemically described as para-toulenesulfonic acid, blocked para-toulenesulfonic acids, and concentrated phosphoric acid. The catalyst are used at very low levels in our formulation as described in the detailed examples.

The concentrations of the acid catalysts used in the examples are preferably from 0.001% to 10 percent and most preferably from 0.001% to 3%. The metal salts in the formulations are used preferably at a level from 0.1% to 8% and most preferably from 0.1% to 5%. The total solids in the formulations preferably range from 1% to 40% and most preferably from 1% to 25%. The crosslinkers in the formulations range preferably from 0% to 25% and most preferably from 0% to 20%.

Preferred cationic surfactants are quaternary ammonium compounds having at least one C8–C20 hydrocarbyl (alkyl, aryl, aralkyl, or cycloalkyl) group; a preferred hydrocarbyl group is a hexadecyl group. The hydrocarbyl functionality may be attached to a quaternary nitrogen atom that is part of a heterocyclic ring system (such as a pyridine, morpholine, or imidazoline ring). A variety of other preferred alternative cationic surfactants are listed as follows: benzalkonium chloride, ahexadecyltrimethylammonium chloride, hexadecyl pyridinium chloride, stearyl trimethyl ammonium chloride, dodecylpyridinium chloride, as well as the corresponding bromides, and a hydroxyethylheptadecylimidazolium halide.

Some other preferred surfactants are glycerol stearates, glycerol oleates, cocoaminopropyl betaine, and polyethylene glycol monostearates. Polyethylene glycols and polyoxypropylene glycols are suitable nonionic surfactants. Also nonylphenol ethoxylates, as well as other ethoxylated acetylenic diols will perform well. Surfactants which contain both polyoxyethylene and polyoxypropylene chains such as the Pluronics® would prove effective for our invention.

A small amount of an anionic surfactant may be added to improve the initial response of the elastomer surface during the damp donning process. A preferred anionic surfactant would be sodium naphthalene sulfonate; alternatives include alkyl benzene sulfonates. Special groups of. surfactants such as the sulfonated non-ionic polyoxyethylene ethers, sodium dodecyl sulfate, sulphosuccinates, phosphate esters, and sodium dodecyl benzene sulfonate would also prove effective for our invention.

The silicone surfactants employed in the present invention are principally polyether modified polydimethylsiloxanes. Examples of such useful silicones are available from OSi Specialties and Dow Corning Corporation. The OSi silicones that were evaluated were from both the NuWet® and SilWet® product lines. NuWet® 100, 300, and 500 were tested. The preferred SilWet® products were SilWet® 7001 and SilWet® 7605. The Dow Corning silicone we examined in the present invention was Dow Corning 365, an amino-modified silicone. Other silicones which would prove effective in the present invention include dimethicone cyclodimethicone (Dow Corning® 245). Also a variety of Silicone based quaternary compounds (Tegopren)® that are available from Goldschmidt would prove effective in the present invention.

Ancillary Information on Silicone Surfactants

Among the silicone surfactants that would prove useful in the invention are included NuWet® 300 and NuWet® 500, both believed to be polyether modified silicones. Also the diquaternary polydimethylsiloxanes Tegopren® 6920 and 6922 have proved useful in our invention. Also the Silwet® 7605 that is also believed to be a polyether modified polydimethysiloxane has proved quite efficient as a silicone surfactant. Another silicone surfactant of use is Dow Corning® 245 that is chemically identified as a decamethylcyclopentasiloxane.

To impart damp slip properties to the flexible elastomeric article, which is at least substantially powderless and is preferably chlorinated, the article is treated with a lubrication composition. Two preferred combinations of components are as follows. The first composition comprises (i.e., having at least) (1) an acetylenic diol and (2) at least one compound selected from the group consisting of an organo-modified silicone, an amino-modified silicone, and a cationic surfactant, preferably, 1-hexadecylpyridinium chloride monohydrate. The second composition comprises (1) a cationic surfactant, preferably 1-hexadecylpyridinium chloride monohydrate, and (2) at least one compound selected from the group consisting of an organo-modified silicone, an amino-modified silicone, and an acetylenic diol. The lubricant composition is preferably an aqueous solution or dispersion.

The compound 1-hexadecylpyridinium chloride monohydrate (CAS No. 6004-24-6) is a commercially available cationic surfactant. Other suitable cationic surfactants include those comprising at least one lipophilic moiety such as an alkyl, aralkyl, aryl, or cycloalkyl group containing 6 to 18 carbon atoms, and a hydrophilic moiety such as a substituted ammonium group (for example, a tetraalkylammonium, pyridinium, or like group). The counterion present should be compatible with the tissue of the wearer; it could be, for example, chloride or other halide.

Preferred cationic surfactants are quaternary ammonium compounds having at least one $C_8$–$C_{18}$ hydrocarbyl (alkyl, aryl, aralkyl or cycloalkyl) group; a preferred hydrocarbyl group is a hexadecyl group. The hydrocarbyl group may be attached to a quaternary nitrogen atom which is part of a heterocyclic ring (such as a pyridine, morpholine, or imidazoline ring).

As previously mentioned, a particularly preferred surfactant is hexadecylpyridinium chloride. Other suitable cationic surfactants include benzalkonium chlorides, hexadecyltrimethylammonium chloride, dodecylpyridinium chloride, the corresponding bromides, a hydroxyethylheptadecylimidazolium halide, coconut alkyldimethylammonium betaine and coco aminopropyl betaine.

Mixtures of surfactants may also be used.

The cationic surfactant, e.g., the preferred cetylpyridinium chloride, concentration is in the range from about 0.05% to about 2.5% by weight. A range from about 0.25% to about 1.50% by weight, for example, 0.5%, cetylpyridinium chloride solution is preferred.

The acetylenic diols useful in the present invention are acetylenic tertiary glycols and the ethylene oxide adducts of acetylenic tertiary glycols. Preferably, the acetylenic diols used in the practice of the invention are structurally represented by the formula:

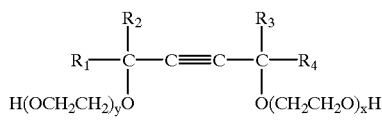

in which $R_1$ and $R_4$ are alkyl radicals containing from 3–10 carbon atoms, and $R_2$ and $R_3$ are selected from the group consisting of methyl and ethyl, and x and y have a sum in the range of 0–60, inclusive, where y=x=0 represents the acetylenic tertiary glycols. In the preferred case, $R_1$ and $R_4$ are alkyl radicals having 3–4 carbon atoms each and $R_2$ and $R_3$ are methyl groups. Further examples and synthesis techniques for the manufacture of these acetylenic diols are disclosed in U.S. Pat. No. 3,268,593 (Carpenter et al.) and U.S. Pat. No. 3,293,191 (Carpenter et al.), which are hereby incorporated by reference.

Acetylenic diols useful in the present invention preferably have a 10-carbon chain as a backbone with a carbon-carbon triple bond in the middle with a hydroxyl group on the carbon atoms on either side of the triple bond. The combination of these groups yields a region of high electron density, making the molecule polar. There is also a symmetrical, highly branched group on each side of this region supplying the molecule with two hydrophobic areas. Overall the molecule has a hydrophobic-hydrophilic-hydrophobic structure, making it a good wetting agent or surface tension reducer. See J. Schwartz et al., "Acetylenic diol-based additives help glove makers meet quality standards," Elastomerics, pages 16–18, December 1989. Suitable acetylenic diols include the following available from Air Products and Chemicals, Inc., Allentown, Pa.: Surfynol® 104 (2,4,7,9-tetramethyl-5-decyn-4,7-diol), Surfynol® 104E (Surfynol® 104/ethylene glycol, 50/50), Surfynol® 440 (Surfynol® 104 +3.5 moles ethylene oxide), Surfynol® 465 (Surfynole 104 +10 moles ethylene oxide) and Dynol® 604 (a mixture of ethoxylated acetylenic diols).

The acetylenic diols are preferably ethoxylated acetylenic diols such as Dynol® 604 and Surfynol® 400 series available from Air Products and Chemical Inc., Allentown, Pennsylvania. Dynol® 604 is preferred because it provides better lubricity. The acetylenic diol is used in the form of a solution, such as an aqueous solution containing at least 0.01% by weight up to, for example, 2% by weight of acetylenic diols. The acetylenic diols may be used in a mixture or combination.

The modified silicones useful in the present invention are hydrophilic, nonionic silicones. Examples of such silicones are commercially available from OSi Specialties, Inc., Danbury, Connecticut are Nuwet® 100, NuWet® 300 and Nuwet® 500. NuWet® 100 is a copolymer described as an organo-modified polydimethylsiloxane, more specifically a polyalkylene oxide modified polydimethylsiloxane. NuWet® 300 is also a copolymer described as an amino-modified silicone-polyether copolymer. As a result of the amino-modification, this material has reportable quantities of an alkanolamine. Nuwet® 500 is a blend of an organo-modified polydimethylsiloxane (>65%) and an ethoxylated alkyl (<20%). There are reportable quantities of ethylene oxide (<20%; upper bound concentration per MSD Sheet is 0.0002%). The following Table provides some physical properties for these three materials.

| Physical Property | NuWet ® 100 | NuWet ® 300 | NuWet ® 500 |
|---|---|---|---|
| Appearance | Clear | Clear-Sl. Haze | Clear |
| Color | Lt. Straw | Lt. Straw to Tan | Colorless to Lt. Straw |
| Nominal Viscosity, cP | 425 | 3500 | 400 |
| Solubility in Water | Soluble | Dispersable | Dispersable |
| Ionic Nature | Non-ionic | Non-ionic | Non-ionic |
| % Actives | 100 | 100 | 100 |
| Density | 1.06 | 1.027 | 1.02 |
| Flash Point[a] | 175° F. | 230° F. | 285° F. |
| Freezing Point | −9.4° F. | <32° F. | <32° F. |
| Molecular Weight | Copolymer | Copolymer | Copolymer |

*Pensky-Martens closed cup ASTM D-93.

According to OSi's product bulletin, the following non-aqueous diluents have been found useful:
 ethylene-propylene oxide polymers (Ucon® 50HB 100, Union Carbide)
 methyl soyate (Emery® 2235, Henkel)
 methyl oleate (Emerest® 2301, Henkel)

methyl cannolate (Emery® 2231, Henkel)
propylene carbonate (Arco)
oleyl alcohol (Novol, Croda)

When preparing aqueous solutions or dispersions with these materials, OSi recommends pouring the silicone into the vortex of the total water while mixing at a moderate speed (about 300 rpm to about 400 rpm). Mixing is continued until a uniform solution or dispersion is obtained. Non-aqueous solutions or dispersions are prepared in a similar manner, but mix at about 150 rpm to about 200 rpm until a clear mixture is obtained.

U.S. Pat. No. 4,690,955 (Kilgour et al.); U.S. Pat. No. 4,769,174 (Kilgour); U.S. Pat. No. 4,847,398 (Mehta et al.) and U.S. Pat. No. 4,857,583 (Austin et al.), disclose various organo-modified polysiloxane copolymers (i.e., organo-modified silicones) and methods of making same. Such copolymers contain hydroxyl groups. The amino-modification may be performed by first substituting a halide for the hydroxyl group. The halide may then be reacted with ammonia or an amine to substitute an amino group for the halide. This latter process is called ammonolysis of halides. Alternatively, amino-modified polysiloxanes (i.e., amino-modified silicones) may be prepared according to U.S. Pat. No. 3,905,823 (Piskoti), which is hereby incorporated by reference. Therein the amino-modified polysiloxanes are prepared by mixing an organo-modified polysiloxane (i.e., organo-modified silicone) with amino-functional silanes or siloxanes and thereafter equilibrating the mixture in the presence of a base catalyst, e.g., alkali metal hydroxides, alkoxides, hydrides, alkyls, alkenyls and aryls, and silanoates.

The modified silicone is generally used in the form of a solution, such as an aqueous solution containing at least 0.05% by weight up to, for example, 5% by weight of the modified silicone.

The lubricant composition need not coat the wearer-contacting surface completely. It is only necessary that enough lubricant composition is applied to enhance damp slip. It is preferred, to the extent that it is practicable, to keep the lubricant composition on the wearer-contacting surface, in the case of medical or dental gloves, in order to ensure that maximum grip is maintained on the outer surface. The lubricant composition can be applied as an aqueous solution containing from about 0.2 to about 2% by weight lubricant composition total. The article can be dipped in such solution or the solution can be sprayed or painted on it, preferably before it is removed from the form. Alternatively, the lubricant composition can be applied after the article is stripped from the form.

It is understood that other substrate polymers in dispersed, e.g., latex, form, including polyurethanes, may not need to be vulcanized like a natural rubber latex in every case, as can be readily appreciated by those skilled in the art.

It also is understood that various optional ingredients may be incorporated in these articles as apparent to those skilled in the art. For example, where the article is a glove, an antiblock agent may be used which would facilitate donning and use. The antiblock agent is preferably a low-melting wax (mp. from about 100° C. to about 150° C.) such as polyethylene wax added as an aqueous emulsion (e.g., 1–2%) to the coating mixture. The particle size of the wax should be preferably less than 1 μm to avoid interference with the surface morphology. Alternatively, anti-blocking agents may be micronized polyethylene or polytetrafluoroethylene.

In accordance with the present invention, an embodiment of a continuous process for making a powder-free glove comprises in summary form:

(i) dip-coating a coagulant onto a glove form;
(ii) dip-coating over the coagulant layer a layer of an elastomer;
(iii) leaching the elastomer article in the hot water;
(iv) priming the elastomer surface of the article while on the glove form, for example, by means of a dilute acid;
(v) rinsing the primed surface in water or aqueous alkali;
(vi) dipping the article, while still on the glove form, in an acrylic-type polymer dispersion and a curing agent therefor;
(vii) heat curing the elastomer and polymer;
(viii) removing the glove from the form, thereby reversing the glove (optional);
(ix) chlorinating the glove;
(x) neutralizing the glove and residual chlorine;
(xi) rinsing the glove;
(xii) (optionally) treating the glove with a lubricant composition;
(xiii) (accordingly optionally) drying the lubricant treated glove; and
(xiv) removing the glove from the form, thereby reversing the glove (if step (viii) not used).

If the elastomer is not to be chlorinated, steps (ix) and(x) can be omitted.

The application of the lubricant solution provides the chlorinated powder-free glove with superior lubricity with respect to wet/damp hand donning.

In an expanded manner, the steps for one embodiment of the present invention are discussed below. First there is a cleaning step to clean for example the hand form, typically made of porcelain, to remove residue from previous manufacturing iterations. The clean form is then dried to remove water residue by conveying the form through a preheated oven to evaporate the water.

The preheated form is then dip-coated in a bath containing a coagulant, a powder source and a surfactant. The coagulant preferably contains calcium ions to break the protection system of the emulsion, thereby allowing the latex to deposit on the form. The powder is preferably a calcium carbonate powder which later acts as a release agent. Alternatively, the powder source may be omitted by using the lipo compound and surfactant combination in the coagulant to aid in stripping the glove according to U.S. Pat. No. 4,310,928 to Joung. The surfactant provides good wetting to avoid forming a meniscus and trapping air between the form and deposited latex, particularly in the cuff area. An example of such a surfactant is an acetylene diol. As noted above, the form has been preheated in the drying step and the residual heat dries off the water leaving calcium nitrate, calcium carbonate powder and surfactant on the surface of the form.

The coated form is then dipped into a latex containing tank. The latex contains for example, natural rubber latex plus stabilizers, antioxidant, activators, accelerators, and vulcanizers, and the latter all being in powder form. The stabilizers are preferably of the phosphate type surfactants. The antioxidants are preferably the phenol type, for example, Antioxidant 2246 (2,2'-methylenebis (4-methyl-6-t-butylphenol)) available from PMC Specialty Group, Fords, N.J. The activator may be for example zinc oxide. The accelerator may be for example dithiocarbamate. The vulcanizer is preferably sulphur or a sulphur-containing compound. If these materials are used, the stabilizer, antioxidant, activator, accelerator and vulcanizer are dispersed into water to avoid crumb formation by using a ball mill or an attritor. This dispersion is then mixed into the latex. An emulsified wax, which is used as an antiozonant, is then added to the latex mixture. The coated form is then dipped into the latex composition with the thickness of the latex deposited thereon controlled by the duration of the dip (in a single dip situation). This is about 5 to about 20 seconds, e.g., about 12 seconds, for a surgical glove; and about 20 to about 70 seconds, e.g., about 50 seconds, for an orthopedic glove.

The form now coated with latex is then dipped into a leaching tank in which hot water is circulated to leach out all water soluble components for example residual calcium nitrates and proteins contained in the natural latex. This leaching process may continue for about twelve minutes with the tank water being about 120° F.

The form is then dipped into a tank containing the acrylic-type resin dispersion containing the curing agent with the thickness of the latex deposited thereon controlled by the duration of the dip (in a single dip situation).

The form is then extracted from the coating tank to a bead and print station. At this station, a bead is formed around the cuff area at the end of the glove by mechanically rolling down the top portion or the end portion of the glove a predetermined amount. Company logos, size and a traceable date of manufacture are then printed onto the exterior of the glove, for example by injecting ink into the latex coating on the form.

The latex/polymer coated form is then sent to a curing station where the natural rubber in the form substrate coating is vulcanized and the polymer is cured typically in an oven, thereby heat curing the rubber and curing the acrylic-type resin. The curing station initially evaporates any remaining water in the coating of the form and then proceeds to the higher temperature vulcanization of the rubber and curing of the acrylic-type resin. The drying may occur between 190° F. to 200° F. with a vulcanization step occurring at temperatures for example from about 220° F. to about 240° F. This overall process may last about forty to forty-five minutes total. For example, the oven may be divided into four different zones with a form being conveyed through the zones of increasing temperature. One example is an oven having four zones with the first two zones being dedicated to drying and the second two zones being primarily the vulcanization step. Each of the zones may have a slightly higher temperature, for example, the first zone at about 180° F., the second zone at about 200° F., a third zone at about 220° F. and a final zone at about 240° F. The residence time of the form within a zone in this case is about ten minutes or so. The accelerator and vulcanizer contained in the latex coating of the form are used to cross-link the natural rubber therein. The vulcanizer forms sulphur bridges between different rubber segments and the accelerator is used to speed up sulphur bridge formation. The resin is crosslinked and covalently bonded to the rubber substrate.

The gloves may be removed from the glove forms and then chlorinated or chlorinated while on the forms. If a continuous process is used, the cured gloves leaving the curing station and optionally still on the form are then chlorinated. The chlorination, or more generally halogenation, may be performed in any suitable manner known to those skilled in the art. Such methods include (1) direct injection of chlorine gas into the water mixture, (2) mixing high density bleaching powder and aluminum chloride in water, (3) brine electrolysis to produce chlorinated water, and (4) acidified bleach. See for example U.S. Pat. No. 3,411,982 (Kavalir), U.S. Pat. No. 3,740,262 (Agostinelli), U.S. Pat. No. 3,992,221 (Homsy, et al.; however, it is modified to treat the wearer-contacting surface rather than or in addition to treating outer surface with chlorine gas), U.S. Pat. No. 4,597,108 (Momose), and U.S. Pat. No. 4,851,266 (Momose). One preferred method is to inject chlorine gas into a water stream and then feed the chlorinated water into a chlorinator (a closed vessel) containing the washed gloves. The concentration of chlorine can be monitored and controlled to control the degree of chlorination. The chlorine concentration is typically at least about 500 ppm, preferably from about 500 ppm to about 1,200 ppm, e.g., about 800 ppm. The time duration of the chlorination step may also be controlled to control the degree of chlorination. The time duration may range from about 3 to about 20 minutes, e.g., 7 minutes. The gloves being in a collapsed state will chlorinate to a greater extent on the outside surface with a lesser amount on the inside surface of the glove.

In another preferred method, the gloves (removed from the forms) may be chlorinated by placing them into a chlorinator, including a front-loaded industrial washer, containing a water bath which contains bleach which is subsequently acidified to a pH of 2 to about 3. The chlorine concentration ranges from about 0.05 to about 0.3 wt. e.g., about 0.1 wt.%. The time duration ranges from about 3 to about 25 minutes. Again, the outside surface of the glove will have a greater amount of chlorination than the inside surface of the glove. The degree of chlorination of the inner and outer surfaces of the glove can be controlled by choosing which side of the glove is on the outside or by repeating the chlorination step or a combination of both inversions of the glove and repeated chlorination.

The acidified bleach is then neutralized preferably with ammonium hydroxide or with sodium thiosulfate. This step neutralizes the acidified water contained in the chlorinator and quenches excess chlorine to ammonium chloride, if ammonium hydroxide is used.

Still within the industrial washer, the chlorinated gloves are then rinsed with tap water at about ambient temperature. This rinse cycle may be repeated as necessary. Once all water is removed from the front-load washer, the gloves are tumbled to drain excess water.

A lubricant solution is then added into the chlorinator containing gloves which are then tumbled for about five minutes. This coats the outside of the glove with the lubricant solution. The lubricant solution is drained from the chlorinator and may be reused. If reused, the lubricant solution is preferably reused once more.

The coated gloves are then put into a drier and dried for about ten to fifteen minutes at about 110° F. to dry the donning surface. The gloves are then reinverted and dried for about twenty-five minutes at about 120° F.

The foregoing shows a sequence of events in the manufacture of gloves according to the present invention.

EXAMPLES

To further the understanding of the invention the following examples are provided as a means of illustration.

Example 1

A surgical glove was processed by submerging the hot form in coagulant, immersing it in a natural rubber latex, leaching it in tap water, acid pretreatment with a two percent sulfuric acid solution, and then overdipping with a solution containing an acrylic latex (Rohm and Haas AC-1024), a melamine crosslinker such as Cymel 303 or Cymel 373, $Al(NO_3)_3$ (a metal salt), and phosphoric acid as an acid catalyst. The coated forms were placed in an oven for 30 minutes at 110° C. The gloves were stripped from the formers and washed with water to remove any particulate material and thoroughly dried. In this example, the gloves were not halogenated. A scale from 1–5 was used to rank the donning performance of the articles generated from Formulations 1–5 where:

TABLE 1

| Rating | Explanation |
|---|---|
| 1 | Tacky; glove difficult to start to don |
| 2 | Poor; glove tends to adhere to hand |
| 3 | Fair; glove goes on with moderate effort |
| 4 | Good; donning with some dress down |
| 5 | Excellent; donning with no dress down |

In each of the following formulations, the ingredients were added in the following order slowly agitating throughout the process. The aluminum nitrate ($Al(NO_3)_3$) was put into the water and agitated until dissolved. The melamine crosslinker (Cymel 303 or Cymel 373) were added to the solution with agitation until dissolved. The resin and phosphoric acid were then added.

| Formulation Number | Composition (Weight Percentage) | Dry Skin Slip |
|---|---|---|
| 1 | Al $(NO_3)_3$ = .95%<br>Rohm & Haas AC-1024 = 15.15%<br>Cymel ® 303 = 2.67%<br>Phosphoric Acid = 0.07%<br>Water = 81.17% | 5 |
| 2 | Al $(NO_3)_3$ = 1.03%<br>Rohm & Haas TR-520 = 15.15%<br>Cymel ® 303 = 2.67%<br>Phosphoric Acid = 0.07%<br>Water = 81.08% | 5 |
| 3 | Al $(NO_3)_3$ = 1.01%<br>Rohm & Haas E-32NP = 15.15%<br>Cymel ® 303 = 2.67%<br>Phosphoric Acid = 0.07%<br>Water = 81.08% | 5 |
| 4 | Al $(NO_3)_3$ = 1.04%<br>Rohm & Haas AC-1024 = 15.15%<br>Cymel ® 373 = 2.67%<br>Phosphoric Acid = 0.04%<br>Water = 81.08% | 5 |
| 5 | Al $(NO_3)_3$ = 1.01%<br>Rohm & Haas TR-520 = 15.15%<br>Cymel ® 303 = 2.67%<br>Phosphoric Acid = 0.07%<br>Water = 81.08% | 5 |

Example 2

Gloves from Formulation 1 in Example 1 were removed from the form after cooling, washed with water, chlorinated, and then treated with a combination of slip agents. The gloves produced were essentially free of powder, non-blocking, soft, and exhibited excellent adhesion up to the break elongation point of the base natural rubber elastomer. The gloves were also found to exhibit good damp and dry slip. In this example, chlorination of the elastomeric articles was performed using the steps of:
(a) rinsing all particulate matter from six coated elastomeric articles with water,
(b) placing the elastomeric articles into a suitable corrosion-resistant container,
(c) adding about 2000 mL water into the container and adding about 12.4 grams of 8.5% active bleach,
(d) agitating the elastomeric articles for about five minutes and subsequently injecting about five grams of concentrated hydrochloric acid,
(e) agitating for about ten minutes more,
(f) adding about twenty grams of 37% ammonium hydroxide and agitate for about five minutes more,
(g) rinsing the gloves thoroughly with water before being immersed and tumbled in a suitable combination of slip agents, and then
(h) tumbling the gloves in a dryer until dry.

Gloves prepared in Example 1 were chlorinated and post-treated with various compositions of slip agents and evaluated with respect to damp skin. The following post-treated gloves from Example 1 were prepared and evaluated for donning with respect to damp. The results of these evaluations are summarized in Tables 2 through 5 (when "%" means weight percent).

Three (3) pairs of gloves were tested for each sample, with each pair donned by a different member of a three-person panel.

TABLE 2

| Sample | CPC | N-500 | Damp Skin Lubricity[a] |
|---|---|---|---|
| 1 | 1.0% | 0.75% | 3/4/4 |
| 2 | 0.50% | 0.50% | 2/3/4 |
| 3 | 0.25% | 0.50% | 3/4/4 |
| 4 | 2.00% | 1.00% | 3/5/4 |
| 5 | 0.50% | 0.10% | 5/4/4 |

[a]first/second/third person's rating.

TABLE 3

| Sample | CPC & BAC | N-500 | Damp Skin Lubricity |
|---|---|---|---|
| 6 | 0.50% & 0.25% | 0.25% | 5/3/4/5 |
| 7 | 0.00% & 0.50% | 0.50% | 2/2/2 |
| 8 | 0.25% & 1.00% | 0.25% | 4/4/3 |
| 9 | 0.25% & 1.00% | 0.50% | 4/3/4 |
| 10 | 0.25% & 0.75% | 0.50% | 5/5/3 |

TABLE 4

| Sample | CPC & BAC | N-300 | Damp Skin Lubricity |
|---|---|---|---|
| 11 | 0.50% & 0.25% | 0.25% | 3/4/3 |
| 12 | 0.00% & 0.50% | 0.50% | 2/3/2 |
| 13 | 0.25% & 1.00% | 0.25% | 3/2/2 |
| 14 | 0.25% & 1.00% | 0.50% | 3/4/3 |
| 15 | 0.25% & 0.75% | 0.50% | 3/3/3 |

TABLE 5

| Sample | CPC and PEO | N-500 | Damp Skin Lubricity |
|---|---|---|---|
| 16 | 1.0% & 1.0% | 0.75% | 3/5/3 |
| 17 | 0.50% & 1.0% | 0.50% | 2/4/3 |

TABLE 5-continued

| Sample | CPC and PEO | N-500 | Damp Skin Lubricity |
|---|---|---|---|
| 18 | 0.25% & 1.0% | 0.50% | 4/2/4 |
| 19 | 2.00% & 1.0% | 1.00% | 4/3/3 |
| 20 | 0.50% & 1.0% | 0.10% | 4/4/4 |

Example 3

In this example, the following ingredients were added in the following order to prepare the resin coating bath composition using slow agitation throughout the preparation process. About 140.67 grams of aluminum nitrate $(Al(NO_3)_3$ was added to about 15,360.24 grams of water. These ingredients were agitated until all the aluminum nitrate went into solution. Then, about 132.08 grams of Cymel® 350 crosslinker was added to the solution and agitated until it went into solution. Thereafter, about 2,526.02 grams of Rohm and Haas Rhoplex® AC-1024 resin and about 9.58 grams of phosphoric acid (85% v/v) were added forming the resin coating bath solution.

Resin coated surgical gloves were made in the same manner as in Example 1, except that the foregoing resin solution was used instead. The coated gloves were then chlorinated according to Example 2. The gloves were then treated with a variety of lubricant compositions each of which was a mixture of a silicone surfactant and at least one organic surfactant. The resulting gloves were then tested for damp donning and rated using the rating system identified in Example 1. The results are given in Table 6, with Table 7 providing a description of the various surfactants used and others that may also be suitable for use in the present invention. In this example, the samples that exhibited the best donning damp and dry slip for those having a lubricant composition of CPC with DC 365 and CPC with Silwet® L-7001.

TABLE 6

| Sample | Silicone Surfactant | Organic Surfactant | Damp Skin Lubricity |
|---|---|---|---|
| 21 | 0.25% DC 365 | 0.5% CPC | 4–5 |
| 22 | 0.1% DC 365 | 0.5% CPC | 4–5 |
| 23 | 0.25% L-7001 | 0.5% CPC/0.1% Patioinic SSL | 4 |
| 24 | 0.1% L-7001 | 0.5% CPC | 4–5 |
| 25 | 0.25% L-7605 | 0.5% Witco VTSC | 4 |
| 26 | 0.5% L-7001 | 0.5% CPC | 4–5 |
| 27 | 1.0% L-7001 | 0.5% CPC | 4–5 |
| 28 | 0.25% L-7605 | 0.5% K5721 | 4 |
| 29 | 0.25% L-7001 | 0.5% CPC | 4–5 |
| 30 | 0.25% L-7605 | 0.5% CPC | 4–5 |
| 31 | 0.25% L-7605 | 0.5% E6075 | 4 |
| 32 | 0.25% L-7001 | 0.5% GLG-7 | 4 |
| 33 | 0.25% L-7001 | 0.5% F160 | 4 |
| 34 | 0.25% L-7001 | 0.5% Mack 007 | 3 |
| 35 | 0.25% L-7001 | 0.5% Crodafos N10 | 4–5 |
| 36 | 0.25% L-7001 | 0.5% Detain PB | 3–4 |
| 37 | 0.25% L-7001 | 0.5% P188C | 4 |
| 38 | 0.25% L-7001 | 0.25% CPC/0.5% Pationic SSL | 4 |
| 39 | 0.25% N-300 | 0.5% Mack 426 | 4 |
| 40 | 0.25% N-300 | 0.75% Mack 426 | 4 |
| 41 | 0.25% N-300 | 2.0% Mack 426 | 4 |
| 42 | 0.1% N-300 | 0.5% CTMAC | 4 |
| 43 | 0.25% N-300 | 0.75% Mackom | 4 |
| 44 | 0.25% N-300 | 0.5% Mackom | 4 |
| 45 | 0.25% L-7001 | 0.5% P122A | 4 |
| 46 | 0.25% L-7001 | 0.5% Crodafos N3 | 4 |
| 47 | 0.25% L-7001 | 0.5% CPC | 4–5 |
| 48 | 0.25% L-7001 | 0.5% CPC | 4–5 |
| 49 | 0.25% L-7001 | 1.0% CTMAC | 3–4 |
| 50 | 0.5% DC 365 | 0.3% CPC/0.2% PSSL | 3–4 |
| 51 | 0.25% DC 365 | 0.3% CPC/0.2% PSSL | 4–5 |

TABLE 7

Listing of Post Processing Slip Ingredients Evaluated

| Product Designation | Product Type | Manufacturer | Composition |
|---|---|---|---|
| Ritasil ® 190 | Polyethersiloxane | RITA Corporation | Dimethicone |
| Ritasil ® 193 | Polyethersiloxane | RITA Corporation | Dimethicone |
| NuWet ® 300 | Aminomodified silicone-polyether copolymer | OSi Specialities | Silicone Polyether |
| NuWet ® 500 | Organomodified Polydimethyl-siloxane | OSi Specialities | Polydimethylsiloxane/Ethoxylated Alkyl Blend |
| Silwet ® L-7001 | Silicone Copolymer | OSi Specialities | Silicone Polyether |
| Silwet ® L-7605 | Silicone Copolymer | OSi Specialities | Silicone Copolymer |
| Dow Corning ® DC 365 | Aminofunctional Siloxane emulsion | Dow Corning | Dimethylsilyl Dimethyl-aminoethyl-aminopropyl Silicone |
| Witcosoft ® 110 | Cationic Surfactant | Witco | Methyl-bis Hydrogenated Tallow Amidoethyl-Ammonium Methyl Sulfate |
| Witcosoft ® 222 LT90 | Cationic Surfactant | Witco | Methyl bis(alkylamido ethyl)-2-Hydroxyethyl Ammonium Methyl Sulfate, Ethoxylated |
| Witcosoft ® 222 PG | Cationic Surfactant | Witco | Methyl Bis(Tallow Amido Ethyl)-2-Hydroxyethyl Ammonium Methyl Sulfate |
| Witcosoft ® 315 | Cationic Surfactant | Witco | Dimethyl Dialkyl (C14–18) Ammonium Chloride |
| Varisoft ® BT85 | Quaternary Ammonium Compounds | Witco | Trimethyl Ammonium Chloride |
| Varisoft ® CSAC | Cationic Surfactants, surfactant blends | Witco | Benzenemethanamin-ium, N,N-Dimethyl-N-Octadecyl-Chloride and Ethoxylated Castor Oil |
| Varisoft ® TSC (VTSC) | Quaternary Ammonium Compounds | Witco | Stearyl Trimethyl Ammonium Chloride |

TABLE 7-continued

Listing of Post Processing Slip Ingredients Evaluated

| Product Designation | Product Type | Manufacturer | Composition |
|---|---|---|---|
| Varisoft ® 442 100P | Quaternary Ammonium Compounds | Witco | Quaterium-18; Diemthyl Di-hydrogenated Tallow Ammonium Chloride |
| Varox ® 1770 | Nonionics | Witco | Cocamidopropylamine Oxide |
| Emcol ® E6075 | Quaternary Ammonium Compounds | Witco | N(Stearoyl Colamine Formyl Methyl) Pyridinium Chloride |
| Kemester ® 5721 | Fatty Acid Ester, Nonionics | Witco | Tridecyl Stearate |
| Witconol ® 2720 | Polysorbate 20, Nonionics | Witco | No data available |
| Witcodet ® 804 | Mixture of Surfactants | Witco | No data available |
| Miranol ® Ultra C32 | Organic Surfactant | Rhone-Poulene | Sodium Cocamphoacetate |
| Geropon ® 99 | Organic Surfactant | Rhone-Poulene | Sodium Dioctyl Sulfosuccinate |
| Mackanate ® OM (Mackem) | Organic Surfactant | McIntyre Group | Disodium Solfosuccinate |
| Rhodafac ® RA-600 | Complex Organic Phosphate Esters | Rhone-Poulenc | Poly(Oxy-1-ethanediyl), Alpha-Hydro-Omega-Hydroxy-, C8–10 alkyl ethers, Phosphate |
| Crodesta ® F-160 | Carbohydrate Fatty Ester | Croda | Sucrose Stearate |
| Crodafos ® N10 | Alkoxy Ether Phosphate, Amine Salt | Croda | Polyoxyethylene(10) Oleyl Ether Phosphate, Amine Salt |
| Crodafos ® N3 Neutral | Alkoxy Ether Phosphate, Amine Salt | Croda | Polyoxyethylene(3) Oleyl Ether Phosphate, Diethanolamine Salt |
| Mackalene ® 426 | Cationic Surfactant | McIntyre Group Inc. | Isostearamidopropyl Morpholine Lactate |
| Pationic ® 122A (PIZZA) | Lactylate | R.I.T.A. Corp. | Sodium Caproyl Lactylate |
| Pationic ® 138C (P138C) | Lactylate | R.I.T.A. Corp. | Sodium Lauroyl Lactylate |
| Pationic ® SSL | Lactylate | R.I.T.A. Corp. | Sodium Stearoyl Lactylate |
| Tergitol ® NP-9 | Nonionic | Union Carbide | Nonyl Phenol Ethoxylate |
| Cetyl Pyridinium Chloride | Quaternary | Spectrum Chemical | Cetyl Pyridinium Chloride |
| Pationic ® CSL | Lactylate | R.I.T.A. Corp. | Calcium Stearoyl Lactylate |
| Benzalkonium Chloride | Cationic | Aldrich | Benzalkonium Chloride |
| Cetyl Trimethyl-ammonium Chloride (CTMAC) | Cationic | Aldrich | Cetyl Trimethyl-ammonium Chloride |
| Poly Ox ® 205 | Polyethylene Oxide | Union Carbide | Polyethylene Oxide |
| Detain ® PB | Betaine | Deforest Products | Betaine |
| Crodafos ® N-3 | Phosphate Esters | Crods | DEA Oleth-3 Phosphate |
| Arcol ® 11-34 | Polyoxypro-pylene ether glycol | Arco | 6000 m.w. Polypropylene Ether Glycol |
| Mac ® k 007 | Polyquat | McIntyre | Polyquaterium-7 |

In Tables 2 through 6, the abbreviations have the following meaning:

| Abbreviation | Explanation |
|---|---|
| CPC | cetylpyridinium chloride |
| BAC | benzalkonium chloride |
| N-500 | NuWet ® 500 |
| N-300 | NuWet ® 300 |
| PEO | Polyethyleneoxide |

Example 4

In accordance with EXAMPLE 1, a glove was produced by dipping the prepared natural rubber latex layer with the following overdip compositions (i.e., the resin coating both composition). This example involved styrene acrylic lattices with urea-formaldehyde or glycoluridil crosslinkers. The only difference from Example 1 was that no acid was used in the leach or as a predip to prepare the natural rubber latex surface. Rather, the acid was included in the formulation itself, thereby eliminating the separate acid step.

In the following formulations, the ingredients were added in the following order to prepare the resin coating bath composition using slow agitation throughout the preparation process. The aluminum nitrate (when present) was added to the water and the mixture agitated until the aluminum nitrate went into solution. Then, the crosslinker (e.g., Beetles® 65, Cymel® 1171 or Cymel® 1172) was added to the solution and agitated until it went into solution. Thereafter, the resin (Rohm and Haas Rhoplex® AC-3094, AC-1024 or AC-2573) and the acid catalyst (Cycat® 4040) were added and agitated. Then the sulfuric acid was added for treating the surface of the natural rubber latex to enhance the covalent bonding of the resin coating to the latex substrate once tiered.

FORMULATION 6

Rohm & Haas AC-3094-68.16 grams
Beetles® 65-12 grams.
Cycat® 4040-0.3 grams
Aluminum Nitrate-4.26 grams
Sulfuric Acid-0.45 grams
Water-565.18 grams

FORMULATION 7

Rohm and Haas AC-1024-68.16 grams
Beetles® 65-6 grams
Cycat® 4040-0.3 grams
Sulfuric Acid-0.9 grams
Aluminum Nitrate-4.26 grams
Water-666.66 grams

FORMULATION 8

Rohm and Haas AC-2573-616.78 grams
Cymel® 1171-108.59 grams
Water-5,114.36 grams
Cycat® 4040-5.00 grams
Sulfuric Acid-20.01 grams

FORMULATION 9

Rohm and Haas AC-2573-616.78 grams
Cymel® 1172-108.59 grams

Water-5,114.36 grams
Cycat® 4040-5.00 grams
Sulfuric Acid-20.00 grams

The elastomeric articles prepared with formulations 6 through 9 above were chlorinated according to Example 2 and treated with a composition of slip agents. The resulting elastomeric articles were soft and exhibited excellent adhesion of the coating even up until break elongation of the base neoprene elastomer. The powderfree post-treated elastomers were non-blocking and exhibited excellent lubricity with respect to damp and dry skin.

Example 5

In accordance with the general procedure of Example 1, Example 5 involved the overcoating of neoprene lattices with acrylic lattices crosslinked with melamines. The neoprene latex formulations were prepared from commercial emulsions such as DuPont Dow Elastomers 671A, 750, and 571. The neoprene (i.e., polychloroprene) latexes were compounded with additives including zinc oxide, thixotropes according to Table 8 with preferred ranges for suitable formulations identified within parenthesis.

The neoprene latex used in the example had the following components:

TABLE 8

| COMPONENTS | PARTS BY WEIGHT (PREFERRED RANGE) |
|---|---|
| DuPONT NEOPRENE LATEX 571 (chlorinated rubber latex emulsion) | 100 (40 TO 150) |
| DARVAN ® SMO (monosodium salt of sulfated methyl oleate) | 3 (1 TO 10) |
| DARVAN ® WAQ (sodium lauryl sulfate) | 1 ( 0.2 TO 5) |
| ZINC OXIDE curative (crosslinker) | 5 (1 TO 20) |
| Antioxidant (Sustane) | 2 (1 TO 10) |
| McNAMEE ® CLAY kaolin (thixotrope) | 10 (2 TO 20) |
| ETHYL TUADS accelerator (tetraethylthiuram disulfide) | 1 (0.2 TO 5) |
| BUTYL NAMATE (sodium dibutyl dithiocarbamate) latex accelerator | 1 (0.2 TO 5) |

A number of other commercial polychlorprene latexes may be used including preferably Neoprene Latexes 671 and 750 also available from DuPont, the formulation above is representative.

An acid treatment step was included as a separate step with the neoprene lattices. The neoprene coated form was submerged in a solution containing two percent sulfuric acid for a period of sixty seconds prior to overcoating with the styrene-acrylic solutions. The coating solutions employed in the invention are detailed below.

FORMULATION 10
Rohm and Haas AC-2573-76.50 grams
Cymel® 303-5.60 grams
Water-465.18 grams
Phosphoric Acid-0.29 grams

FORMULATION 11
Rohm and Haas AC-1024-76.50 grams
Cymel® 303-5.60 grams
Water-465.18 grams
Phosphoric Acid-0.29 grams Formulation 10 was chlorinated and treated with an aqueous surfactant of 0.5% cetylpyridinium chloride and 0.25% dimethicone. Formulation 11 was chlorinated and also treated with an aqueous solution of dimethicone. The elastomeric articles were soft and exhibited excellent adhesion of the coating even up until break elongation of the base neoprene elastomer. The powderfree post-treated elastomers were non-blocking and exhibited excellent lubricity with respect to damp and dry skin.

The present invention has been described primarily with respect to surgeon's gloves. As earlier noted, the present invention is also applicable to other skin- or tissue-contacting flexible elastomeric articles, such as condoms, gloves used by doctors and veterinary surgeons for examination purposes (such gloves often being donned with dry hands), catheters, ureters, sheets, sheaths and sheath-type incontinence device.

When the present invention is used for articles such as ureters and catheters, the outer surface is coated with the lubricant composition (this being the wearer-contacting surface); for condoms the inner and/or outer surface may be treated with the lubricant composition.

What is claimed is:

1. A method of treating an elastomeric flexible article, the method comprising:

coating the article surface with a hydrophobic acrylic-type styrene resin having a high modulus relative to natural rubber to form a coating on the article surface;

curing the acrylic-type styrene resin coating halogenating at least one surface of the article;

neutralizing the article surface and residual chlorine; and treating the article surface with a lubricant composition, wherein the lubricant composition is selected from the group consisting of a first composition, a second composition, and a third composition, wherein the first composition comprises
a cationic surfactant and
at least one compound selected from the group consisting of
an acetylenic diol,
an organo-modified silicone,
an amino-modified silicone,
an anionic surfactant, and
a nonionic surfactant, wherein the second composition comprises
an anionic surfactant and
at least one compound selected from the group consisting of
an acetylenic diol,
an organo-modified silicone,
an amino-modified silicone,
a cationic surfactant, and
a nonionic surfactant, and wherein the third composition comprises
a nonionic surfactant and
at least one compound selected from the group consisting of
an acetylenic diol,
an organo-modified silicone,
an amino-modified silicone,
a cationic surfactant, and
an anionic surfactant.

2. A method according to claim 1, wherein the cationic surfactant is 1-hexadecylpyridinium chloride monohydrate.

3. A flexible elastomeric article having a wearer-contacting surface on which a lubricant composition has been applied to improve the lubricity of the surface with respect to the wearer's skin, wherein:

the wearer-contacting surface underlying the lubricant composition comprises a hydrophobic acrylic-type styrene resin having a high modulus relative to natural rubber, the hydrophobic acrylic-type styrene resin being formed into a coating; and the lubricant composition is selected from the group consisting of a first composition, a second composition, and a third composition, wherein the first composition comprises
 a cationic surfactant and
 at least one compound selected from the group consisting of
  an acetylenic diol,
  an organo-modified silicone,
  an amino-modified silicone,
  an anionic surfactant, and
  a nonionic surfactant, wherein the second composition comprises
 an anionic surfactant and
 at least one compound selected from the group consisting of
  an acetylenic diol,
  an organo-modified silicone,
  an amino-modified silicone,
  a cationic surfactant, and
  a nonionic surfactant, and wherein the third composition comprises
 a nonionic surfactant and
 at least one compound selected from the group consisting of
  an acetylenic diol,
  an organo-modified silicone,
  an amino-modified silicone,
  a cationic surfactant, and
  an anionic surfactant.

4. An article according to claim 3, wherein the article is a surgical glove.

5. An article according to claim 4, wherein the cationic surfactant is 1-hexadecylpyridinium chloride monohydrate.

6. A flexible article displaying slip properties with respect to mammalian tissue without use of powder lubricants comprising:

a substrate layer comprising an elastomeric material, the layer having a wearer-contacting surface;

a coating formed on the wearer-contacting surface of the substrate layer, the coating comprising a hydrophobic acrylic-type styrene resin having a high modulus relative to natural rubber; and a lubricant composition applied to the wearer-contacting surface over the coating, wherein the lubricant composition is selected from the group consisting of a first composition, a second composition, and a third composition, wherein the first composition comprises
 a cationic surfactant and
 at least one compound selected from the group consisting of
  an acetylenic diol,
  an organo-modified silicone,
  an amino-modified silicone,
  an anionic surfactant, and
  a nonionic surfactant, wherein the second composition comprises
 an anionic surfactant and
 at least one compound selected from the group consisting of
  an acetylenic diol,
  an organo-modified silicone,
  an amino-modified silicone,
  a cationic surfactant, and
  a nonionic surfactant, and wherein the third composition comprises
 a nonionic surfactant and
 at least one compound selected from the group consisting of
  an acetylenic diol,
  an organo-modified silicone,
  an amino-modified silicone,
  a cationic surfactant, and
  an anionic surfactant.

7. An article according to claim 6, wherein the article is a surgical glove.

8. An article according to claim 6, wherein the cationic surfactant is 1-hexadecylpyridinium chloride monohydrate.

9. An article according to claim 6, wherein the elastomer is selected from the group consisting of natural rubber, a polyurethane, a homopolymer of a conjugated diene, a copolymer of at least two conjugated dienes, a copolymer of at least one conjugated diene and at least one vinyl monomer, and combinations thereof.

10. An article according to claim 9, wherein the elastomer is natural rubber.

11. An article according to claim 9, wherein the elastomer is a polyurethane.

12. An article according to claim 9, wherein the article has a first elastomeric layer and a second elastomeric layer and wherein the elastomer for the first elastomeric layer is natural rubber and the elastomer for the second elastomeric layer is polyurethane.

13. An article according to claim 9, wherein the elastomer is a homopolymer of a conjugated diene.

14. An article according to claim 9, wherein the elastomer is a copolymer of at least one conjugated diene and at least one vinyl monomer.

15. An article according to claim 13, wherein the conjugated diene is isoprene.

16. An article according to claim 13, wherein the elastomer is neolrene.

17. An article according to claim 16, wherein the elastomer is nitrile rubber.

18. An article according to claim 16, wherein the elastomer is a styrene-isoprene-styrene block copolymer.

19. An article according to claim 16, wherein the elastomer is a styrene-butadiene-styrene block copolymer.

* * * * *